United States Patent [19]

Heymes et al.

[11] 4,065,459
[45] Dec. 27, 1977

[54] PROCESS FOR THE PREPARATION OF THIENO(3,2-C) PYRIDINE AND DERIVATIVES THEREOF

[75] Inventors: Alan Heymes, Portet sur Garonne; Jean-Pierre Maffrand, Toulouse, both of France

[73] Assignee: Parcor, Paris, France

[21] Appl. No.: 655,966

[22] Filed: Feb. 6, 1976

[30] Foreign Application Priority Data
May 30, 1975 France .................... 75.17009

[51] Int. Cl.$^2$ ............................................. C07D 283/00
[52] U.S. Cl. ........................... 260/294.8 C; 424/256
[58] Field of Search ......................... 260/294.8 C

[56] References Cited
U.S. PATENT DOCUMENTS

| | | | |
|---|---|---|---|
| 3,969,358 | 7/1976 | Amselem | 260/294.8 C |
| 3,983,125 | 9/1976 | Amselem | 260/294.8 C |

*Primary Examiner*—Alan L. Rothman
*Attorney, Agent, or Firm*—Young & Thompson

[57] ABSTRACT

This invention relates to a process for the preparation of compounds having the formula:

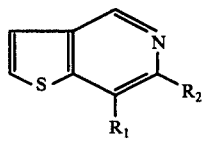

(I)

in which $R_1$ is H or lower alkyl and $R_2$ is H or lower alkyl, or phenyl or benzyl optionally substituted with at least one halogen or a lower alkyl, lower alkoxy, trifluoromethyl or nitro group.

According to this method, a compound of the formula:

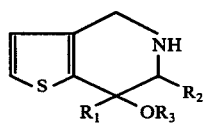

(II)

in which $R_1$ and $R_2$ are as defined above and $R_3$ is H or optionally substituted alkyl or benzyl, is reacted with a derivative Hal—SO$_2$—R (III) in which Hal is halogen and R is optionally substituted alkyl, aryl or aralkyl, to give a derivative of the formula:

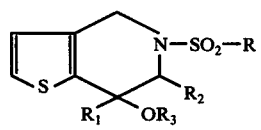

(IV)

in which the various symbols have the above-defined meanings, and the sulfonated derivative of the formula (IV) is heated in the presence of an acid, to give the compound of the formula (I).

6 Claims, No Drawings

PROCESS FOR THE PREPARATION OF THIENO(3,2-c) PYRIDINE AND DERIVATIVES THEREOF

This invention relates to a new process for the preparation of thieno(3,2-c)pyridine and derivatives thereof, having the following formula:

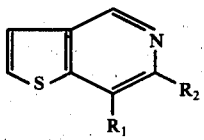
(I)

in which $R_1$ represents hydrogen or a lower alkyl group and $R_2$ represents hydrogen, a lower alkyl group, or a phenyl or benzyl group optionally substituted with at least one halogen atom or a lower alkyl, lower alkoxy, trifluoromethyl or nitro group.

By "lower alkyl or alkoxy" groups are meant here groups containing 1–6 carbon atoms.

Methods for the preparation of thieno(3,2-c)pyridine have been described by many authors, but it has never been possible to develop an inexpensive synthetic process providing the derivative product in good yields.

Thus, L. H. Klemm, J. Shabtoy, D. R. Mc Coy and W. K. Kiang (Heterocyclic Chem., 5, 883, 1968 & ibid., 6, 813, 1969) described a synthesis of 1-benzylthio-2-(4-pyridyl)ethane via thermolysis at 600° C, in poor yields.

S. Gronowitz & E. Sandberg (Arkiv. Kemi., 32, 217, 1970, & ibid., 32, 249, 1970) effected the synthesis of the derivative of the formula (I) from 2-thiophene carboxaldehyde via a four-step procedure difficultly applicable on an industrial scale.

The object of the present invention is to provide an inexpensive process for the production, in good yields, of thieno(3,2-c)pyridine and derivatives thereof having the above-defined formula (I), which are valuable intermediates in the chemical industry and the pharmaceutical industry.

The process of this invention comprises reacting a compound of the formula (II):

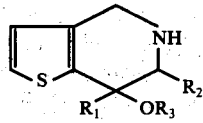
(II)

in which the radicals $R_1$ and $R_2$ have the above-defined meanings and $R_3$ represents hydrogen or an optionally substituted alkyl or benzyl radical, with a halosulfonated derivative of the formula

Hal—SO$_2$—R (III)

in which Hal represents halogen and R represents an optionally substituted alkyl, aryl or aralkyl group, to give a N-substituted derivative having the formula (IV):

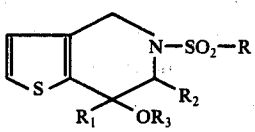
(IV)

in which the various symbols have the above-defined meanings, and heating the sulfonated derivative of the formula (IV) in the presence of an acid, to give the compound of the formula (I).

The substitution reaction with the halosulfonated derivative of the formula (III) (Schotten-Baumann reaction) is generally conducted within an organic solvent, such as methylene chloride or chloroform and in the presence of a binding agent for the hydrohalic acid released during the reaction, typically an alkali metal carbonate such as potassium carbonate, for example.

Examples of derivatives of the formula (III) include methane sulfonyl chloride, trichloromethane sulfonyl chloride, trifluoromethane sulfonyl chloride, benzene sulfonyl chloride, paratoluene sulfonyl chloride, m.acetylbenzene sulfonyl fluoride and p. bromophenyl sulfonyl chloride.

Refluxing the sulfonated compound of the formula (IV) during a period of time of 3–6 hours, dissolved in an organic solvent such as dioxan or a lower alkanol such as ethanol or propanol, and in the presence of a strong inorganic acid such as hydrochloric acid or hydrobromic acid, for example, gives the desired compound of the formula (I).

The starting compounds of the formula (II) and their preparation are described:

a. in the case of the derivatives in which $R_1$, $R_2$ and $R_3$ represent hydrogen, in French patent application No. 74 24 631, filed July 16, 1974, b. in the case of the derivatives in which $R_3$ represents an alkyl or benzyl radical, in French patent application No. 75 16635, filed May 28, 1975.

The following non-limiting Examples are given to illustrate the invention.

EXAMPLE 1

Preparation of thieno(3,2-c)pyridine from 7-methoxy-4,5,6,7-tetrahydro-thieno(3,2-c)pyridine To a vigorously stirred mixture of 102.75 g (0.5 mole) 7-methoxy-4,5,6,7-tetrahydro-thieno(3,2-c)pyridine hydrochloride, 172.5 g (1.25 mole) potassium carbonate, 250 ml water and 750 ml methylene chloride is added, over 20 minutes, a solution of 95.25 g (0.5 mole) tosyl chloride in 700 ml methylene chloride. The reaction medium is then vigorously stirred at room temperature, during two hours. The aqueous phase is decanted and extracted with methylene chloride. The combined organic phases are washed with a saturated sodium chloride solution, dried over sodium sulfate and concentrated in vacuo, to give 156.5 g of the sulfonated compound of the formula (IV) (M.p. = 120° C. Yield = 97%).

A mixture of 10 g(0.031 mole) of the previously obtained sulfonated compound, 30 ml 12N hydrochloric acid and 175 ml dioxan is refluxed during 3 hours, under a nitrogen atmosphere. The organic phase is decanted and concentrated in vacuo. The residue is combined with the aqueous phase and the resulting solution is extracted with isopropyl ether, made basic with a concentrated sodium hydroxide solution and again extracted with methylene chloride. The methylene chloride fractions are washed with a saturated sodium chloride solution, dried over sodium sulfate and then concentrated in vacuo. Distillation of the residue gives 2.6 g thieno(3,2-c)pyridine (B.p./0.2 mm Hg = 72° C. M.p. <50° C. Yield = 63%).

EXAMPLE 2

Using the same procedure, there are obtained:

Thieno(3,2-c)pyridine, from 7-hydroxy-4,5,6,7-tetrahydrothieno(3,2-c)pyridine.

EXAMPLE 3

6-Methyl-thieno(3,2-c)pyridine (M.p. = 70° C), from 7-methoxy-6-methyl-4,5,6,7-tetrahydro-thieno(3,2-c)pyridine.

EXAMPLE 4

7-Methyl-thieno(3,2-c)pyridine (M.p. < 50° C) from 7-methoxy-7-methyl-4,5,6,7-tetrahydro-thieno(3,2-c)pyridine.

| Analysis: for $C_8H_7NS$ | C | H | N |
|---|---|---|---|
| Calculated % : | 64.39 | 4.73 | 9.39 |
| Found % : | 64.51 | 4.62 | 9.65 |

EXAMPLE 5

6-Phenyl-thieno(3,2-c)pyridine (M.p. = 105° C) from 7-methoxy-6-phenyl-4,5,6,7-tetrahydro-thieno(3,2-c)pyridine.

| Analysis: for $C_{13}H_9NS$ | C | H | N |
|---|---|---|---|
| Calculated % : | 73.90 | 4.30 | 6.63 |
| Found % : | 74.13 | 4.28 | 6.48 |

EXAMPLE 6

6,7-Dimethyl-thieno(3,2-c)pyridine (B.p./0.5 mm Hg = 128° C) from 6,7-dimethyl-7-methoxy-4,5,6,7-tetrahydro-thieno(3,2-c)pyridine.

| Analysis: for $C_9H_9NS$ | C | H | N |
|---|---|---|---|
| Calculated % : | 66.22 | 5.56 | 8.58 |
| Found % : | 65.99 | 5.71 | 8.66 |

We claim:

1. Process for the preparation of compounds having the formula:

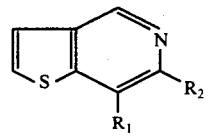

(I)

in which $R_1$ is selected from the group consisting of hydrogen and the alkyl groups having 1–6 carbon atoms and $R_2$ is selected from the group consisting of hydrogen and the lower alkyl groups having 1–6 carbon atoms, comprising reacting at room temperature in methylene chloride or chloroform as a solvent and in the presence of a hydrohalic acid binding agent, a compound of the formula (II):

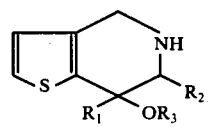

(II)

in which the radicals $R_1$ and $R_2$ having the above-defined meanings and $R_3$ is selected from the group consisting of hydrogen, an alkyl group, a substituted alkyl group, a benzyl radical and a substituted benzyl radical, with a halosulfonated derivative of the formula:

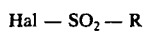

$$Hal - SO_2 - R \quad (III)$$

in which Hal represents halogen and R is selected from the group consisting of the alkyl groups, the substituted alkyl groups, the aryl groups, the substituted aryl groups, the aralkyl groups and the substituted aralkyl groups, to give a N-substituted derivative having the formula:

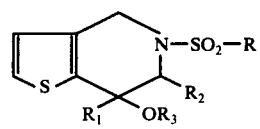

(IV)

in which the various symbols having the above-defined meanings and heating the sulfonated derivative of the formula (IV) in an organic solvent selected from dioxane and the lower alkanols at refluxing temperature in the presence of an acid, to give the compound of the formula (I).

2. Process as claimed in claim 1, wherein the hydrohalic acid binding agent is an alkali metal carbonate.

3. Process as claimed in claim 2, wherein said alkali metal carbonate is potassium carbonate.

4. Process as claimed in claim 1, wherein said lower alkanol is selected from the group consisting of ethanol and propanol.

5. Process as claimed in claim 1, wherein said acid is a strong mineral acid.

6. Process as claimed in claim 5, wherein said acid is selectd from the group consisting of hydrochloric acid and hydrobromic acid.

* * * * *